United States Patent [19]

Weissler

[11] Patent Number: 5,046,508
[45] Date of Patent: Sep. 10, 1991

[54] SYRINGE WITH RETRACTABLE NEEDLE

[76] Inventor: Jonathan Weissler, 584 Hanna, Birmingham, Mich. 48009

[21] Appl. No.: 452,727

[22] Filed: Dec. 19, 1989

[51] Int. Cl.⁵ ............................................. A61B 5/00
[52] U.S. Cl. .................................. 128/763; 604/182; 604/198
[58] Field of Search ....................... 128/763, 765, 770; 604/192, 194, 196, 198

[56] References Cited

U.S. PATENT DOCUMENTS

| 4,027,608 | 6/1977 | Arbuckle | 606/182 |
| 4,813,426 | 3/1989 | Haber et al. | 128/763 |
| 4,838,863 | 6/1989 | Allard et al. | 604/198 |
| 4,900,310 | 2/1990 | Ogle | 604/198 |

FOREIGN PATENT DOCUMENTS

8904141  5/1989  World Int. Prop. O. .......... 128/763

Primary Examiner—Max Hindenburg
Attorney, Agent, or Firm—Dykema Gossett

[57] ABSTRACT

A medical instrument comprises a needle which is movable between an extended operative position where the needle is exposed for use and a retracted inoperative position where the needle is covered so as to reduce the likelihood of inadvertent contact with the needle. The instrument also includes a needle biasing means which normally urges the needle toward its retracted position and an actuator movable between a position of interference with movement of the needle to its retracted position and a position out of interference with the needle to permit the needle biasing means to act on the needle and urge the same toward its retracted position.

17 Claims, 2 Drawing Sheets

SYRINGE WITH RETRACTABLE NEEDLE

FIELD OF THE INVENTION

The present invention relates in general to new and useful improvements in medical instruments having needles, and more particularly to medical instruments with needles wherein the needles are retractable into housings of the instruments after use thereby decreasing the risk of inadvertent contact with the needles by medical and waste-disposal personnel.

BACKGROUND OF THE INVENTION

A number of instruments are currently used for various forms of venepuncture and subcutaneous and intra-muscular injection.

For example, a medical instrument commonly referred to as a "syringe" comprises a cylindrical receptacle carrying a piston, and a needle with a hub threadably mounted on an end of the receptacle. So mounted, the needle is fixed in place relative to the receptacle. The syringe is most often used for drawing blood and for providing subcutaneous and intramuscular injections.

Another medical instrument, termed a "vaccutainer," is primarily used to take multiple samples of blood. A syringe, as stated above, can also be used to sample blood. However, a syringe is only suited to draw a single sample of generally no more than 20 cc of blood. Oftentimes, it is necessary to take multiple blood samples, for example, when a multiplicity of blood tests must be performed on a patient. A vaccutainer can be used to take multiple blood samples upon a single puncture of the patient, thereby reducing patient stress which would otherwise result from the use of syringes and multiple punctures.

The vaccutainer includes a needle attached to a plastic receptacle. Both ends of the needle are exposed. One end is adapted to be inserted into a patient's vein. The other end is adapted to be inserted through a rubber stopper capping a vacuum-sealed glass tube. Upon insertion of the needle through the stopper, blood is drawn from the vein into the tube. When the tube is filled with blood, the tube is removed from engagement with the needle and replaced with another vacuum-sealed tube. In this manner, multiple sample tubes of a patient's blood may be obtained upon a single puncture.

In addition, an instrument known as a "butterfly needle" consists of a needle which is continuous at one end of the needle with a thin diameter rubber tubing. The tubing is adapted to be attached to a syringe, a vaccutainer tube, or any one of a variety of other collection receptacles. The free end of the needle is adapted to be inserted into a patient. The needle carries a plastic fitting having a pair of oppositely projecting "wings" for use in guiding the needle, hence the name "butterfly." The butterfly needle and its associated tubing and receptacle are most often used for collecting blood.

A further example of a medical instrument, termed an "I.V. (intravenous) catheter" is generally used for administering replacement fluids, such as saline solutions, lactated ringer's solution, dextrose water solutions and blood by transfusion.

The I.V. catheter consists of an I.V. placement unit comprising a needle having permanently affixed on one end thereof a plastic handle. A thin plastic sheath having its own plastic handle slidably receives the needle. The sheath extends substantially the entire length of the needle. In use, once the needle with surround sheath have been inserted into a patient's vein, the needle is removed, leaving the sheath behind inside the vein. The needle with its handle is then discarded. A line of rubber tubing is mounted on the handle of the sheath, the free end of the rubber tubing being connected to an I.V. bag.

Although the above-described medical instruments may be effective for performing various forms of venepuncture and subcutaneous and intra-muscular injections, they are associated with a common disadvantage. The problem arises from the lack of a safe and effective method of needle removal and disposal, a problem with which medical institutions, medical personnel, waste disposal personnel and others have become acutely aware as a result of the relatively recent heightened publicity surrounding Hepatitis and the uniformly-fatal disease, "Aquired Immune Deficiency Syndrome (AIDS)."

Several methods of needle disposal are currently used in medical environments, none of which have been demonstrated as being sufficiently safe for medical personnel and waste removal workers, as each of these methods may result in inadvertent contact or puncture by a contaminated needle.

One method of contaminated need disposal requires transportation of, for example, a syringe with attached contaminated needle to a cardboard "needle box" and cutting the needle over the box with a clipper to thereby detach the needle from the syringe proper, the needle then dropping into the box. This method has been demonstrated to be ineffective due to the danger of micro-aerosol spray when the needle is clipped. Moreover, there exists an inherent danger in carrying the exposed needle to the box, as well as disposing of a box filled with contaminated needles. In addition, contaminated needles invariably slip out of the box through seams at folded edges of the paperboard box, and thus present a further danger.

Other dirty needle boxes are currently used. For example, a plastic bucket with hinged lid is commonly in use. Although use of this box eliminates the possibility of leakage of contaminated needles from the box, as there are no open seams through which the needles can pass. However, the inherent dangers associated with carrying needles to the box and micro-aerosol spray (if needles are cut) remain.

Other methods of disposing of contaminated needles consist of either (1) throwing the entire syringe or other like medical instrument with the needle attached thereto into a needle box, or (2) recapping the needle, removing it from the syringe proper, and throwing it into a box. The latter method is the most dangerous. However, in either case, transporting a capped or uncapped needle to a designated container has proven to be both cumbersome and a constant health hazard to both medical institutions and medical and other personnel.

Further, needles are inadvertently thrown into regular waste bins. This poses a constant danger to housekeeping personnel as well as contributing to increased insurance costs of medical institutions.

Therefore, it is obvious that, until the use of needles becomes obsolete, methods and devices directed to reducing the likelihood of inadvertent contact with contaminated needles must be developed.

It has thus been desirable to provide a medical instrument of the type described below in detail comprising a needle which is retractable with respect to the medical instrument so as to reduce the likelihood of accidental contact of personnel with the needle after its use.

SUMMARY OF THE INVENTION

According to the present invention, a medical instrument comprises a needle and a means for mounting the needle for movement between an extended operative position relative to the medical instrument where the needle is exposed for use and a retracted inoperative position where the needle is covered so as to reduce the likelihood of inadvertent contact with the needle.

The mounting means comprises support means, needle biasing means, actuating means and actuator biasing means.

The support means mounts the needle between its extended and retracted positions. The needle biasing means is interposed between the support means and the needle and normally urges the needle to its retracted position. The actuating means is mounted on the support means for movement between inner and outer positions and is adapted to be disposed to retain the needle in its extended position in the inner position of the actuating means. The actuator biasing means is interposed between the actuating means and the support means and normally urges the actuating means toward its inner position of interference with movement of the needle to its retracted position. Movement of the actuating means to its outer position, against the biasing force of the actuator biasing means, disposes the actuating means out of a position of interference with the needle so as to permit the needle biasing means to act on the needle and dispose the same in its retracted position.

BRIEF DESCRIPTION OF THE DRAWINGS

The invention will now be described with reference to the drawings in which.

DESCRIPTION OF THE PREFERRED EMBODIMENTS

Prior to discussing the various concepts of the invention, it is appropriate to review, by way of illustration, a conventional prior art syringe, as the embodiments of the invention to be discussed have been presented in the form of a syringe. It is contemplated, however, that the various concepts of the invention may be in the form of a vaccutainer or any other medical instrument of the type discussed or suggested above.

Figures 1, 4, 5:
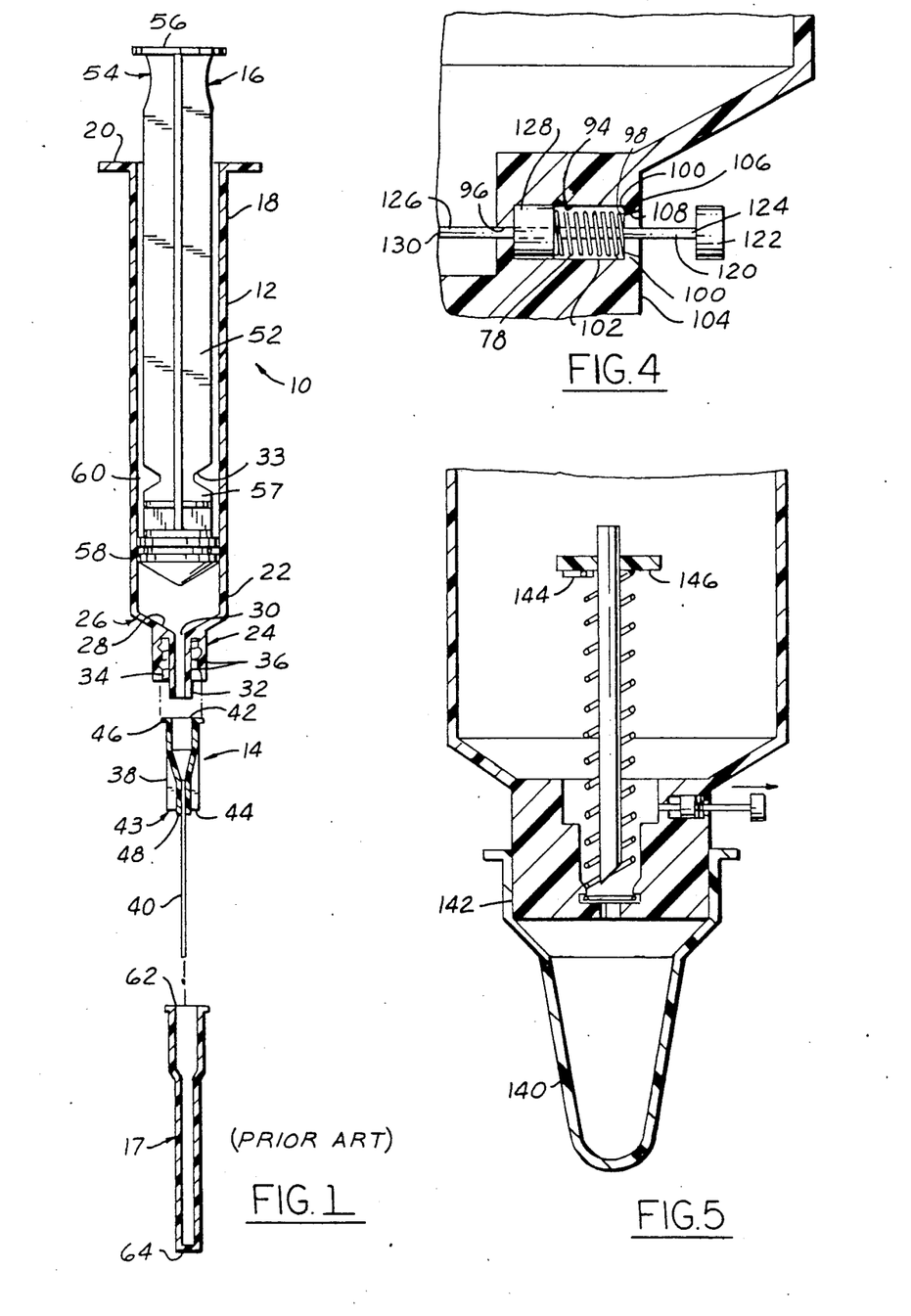
FIG. 1 is an exploded sectional view of a prior art showing of a syringe, needle for the syringe and a cover for the needle.
FIG. 4 is an enlarged fragmentary longitudinal sectional view of that portion of the instrument of FIG. 2 circled and labled "B"
FIG. 5 is an enlarged fragmentary longitudinal sectional view of the instrument shown in FIG. 2, but with the needle thereof illustrated in its retracted position.

Referring to the drawings in detail, and in particular to FIG. 1, there is illustrated a conventional syringe generally indicated by numeral 10. The syringe includes a receptacle 12, a needle unit 14, a plunger 16 and a cover 17.

The receptacle 12 is a hollow cylindrical member and has formed at an upper end 18 thereof a lateral flange 20 extending about the receptacle. The flange 16 functions as a handle or grip during operation of the syringe as is well known by one of ordinary skill in the relevant art. A lower end 22 of the receptacle 12 terminates in a reduced diameter portion 24 by virtue of inclined wall 26 of the receptacle. A transverse inner wall 28 separates the receptacle 12 and the reduced diameter portion 24 at the inclined wall 26 and includes a central opening 30 extending through the inner wall 28. A hollow tubular portion 32 extends downwardly from the inner wall 28 and communicates with an interior 33 of the receptacle 12 through the opening 30. An interior surface 34 of the reduced diameter portion has formed thereon a plurality of threads 36 which function to mount the needle unit 14 on the receptacle 12, as will be discussed below.

The needle unit 14 comprises a hubor carrier 38 and a needle 40. The carrier 38 is a hollow member open at a first end 42 thereof and closed at a second end 43 of the carrier by wall 44. As stated above, the needle unit 14 is adapted to threadably mount on the receptacle 12. To this end, the carrier 38 includes an annular flange 46 at the first end 42 of the carrier and adapted to engage the threads 36 on the interior surface 34 of the reduced diameter portion 24 of the receptacle 12 to removably mount the needle unit 14 on the receptacle.

The needle 40 is fixedly mounted on the carrier 38 at the wall 44 thereof in registry with a hole 48 extending therethrough. When the needle unit 14 is mounted on the receptacle 12 in the manner described above, the needle 40 is set in registry with the tubular member 32, the opening 30 and thus interior 33 of the receptacle 12. In this manner, communication of fluids between the needle 40 and the receptacle 12 is achieved.

The plunger 16 includes a stem 52 carrying at one end 54 thereof a plate portion 56 and at the other end 57 thereof a rubber sealing portion 58. The plunger 16 is mounted on and within the hollow receptacle 12 and is moveable relative thereto in outer and inner directions, with the rubber sealing portion maintaining continuous sealing contact with interior wall 60 of the receptacle 12 as the plunger 16 is moved in either of such directions.

The syringe cover 17 is formed by a hollow cylindrical member which is open at one end 62 thereof and closed at the other end 64 of the cover. The cover 17 is adapted to mount on the needle unit 14 over the needle 40 and to this end the hollow cylindrical cover 17 has an internal diameter which is slightly greater than the external diameter of the carrier 38. In this manner, the cover 17 is adapted to slidably mount over the needle unit in snug-fit relationship relative thereto.

In assembly and operation of the syringe 10 when, for example, it is desired to employ the syringe to draw blood from a patient, the needle unit 14 is mounted on the receptacle 12 in the manner described above by connecting the carrier 38 of the needle unit to the reduced diameter portion 24 of the receptacle with the annular flange 46 of the carrier 38 being set in engagement with the threads 36 of the reduced diameter portion. In this manner, the needle unit 40 is fixedly mounted on the receptacle 12. With the plunger 16 in full registry with the receptacle 12, the needle unit 40 is then inserted into a vein of a patient and the plunger is subsequently moved in the outer direction through forces exacted on the plate portion 56, thereby creating a vacuum within the receptacle and thus effecting withdrawal of blood from the patient. After a sufficient sample of blood has been taken, the needle 40 is withdrawn from the patient. The needle is then inserted into a stopper sealing a tube where the blood sample is stored for subsequent laboratory testing. The the syringe 10 is discarded.

However, prior to discarding the syringe 10, the cap 17 may be mounted on the needle unit 14 in the above-described manner to cover the needle 40 so as to prevent inadvertent contact therewith by health care and waste removal workers. Alternatively, the needle may be detached by cutting the needle over a "dirty-needle" box in the manner discussed above. These methods of needle disposal, however, as stated above, are not sufficiently effective to avoid inadvertent contact with the contaminated needle. In placing the cap 17 over the needle 40, a hurried health care worker may incur contact with the needle. In addition, the potential danger of micro-aerosol spray exists when a contaminated needle is cut.

The potential dangers that are presented by a conventional syringe result from the fact that the syringe employs a needle which is fixed relative to a receptacle of the syringe and is thus in a position to be contacted inadvertently by health care and waste removal workers after use of the instrument.

To reduce the likelihood of inadvertent contact with the contaminated needle by health care and waste disposal workers, the medical instrument according to the present invention employs a needle which is attached to the instrument and exposed when is use, but which is adapted to be set in a retracted position after its use with respect to the instrument so as to reduce the likelihood of accidental contact of personnel with the needle.

As stated above, the various concepts of the invention are shown and described as being embodied in the form of a syringe. However, it is to be understood that such concepts may also be in the form of a vaccutainer or other medical instrument effective for performing various forms of venepuncture and subcutaneous intramuscular injections.

Figure 2:
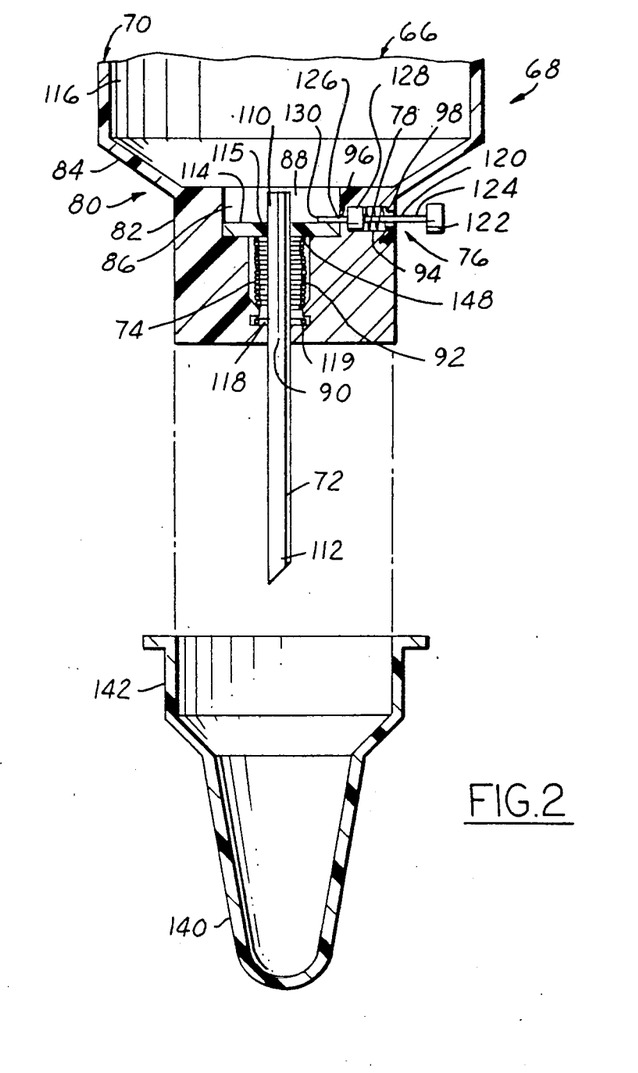
FIG. 2 is an enlarged fragmentary longitudinal sectional view taken through the needle receiving end of a medical instrument in accordance with the invention with a needle thereof illustrated in its extended position.
Figure 3:
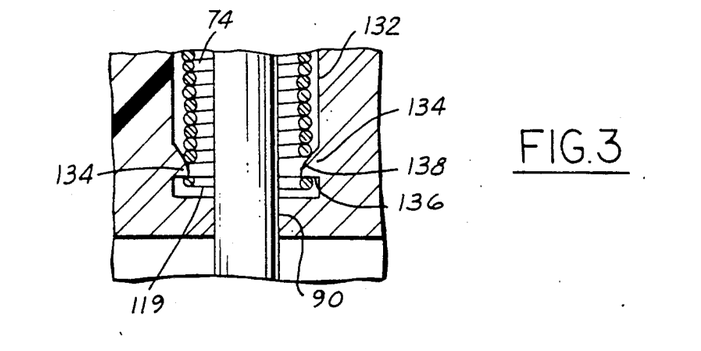
FIG. 3 is an enlarged fragmentary longitudinal sectional view of that portion of the instrument of FIG. 2 circled and labled "A"

Referring specifically to FIGS. 2 and 3, the medical instrument in accordance with the invention comprises a syringe generally indicated by reference numeral 66. Only a lower end 68 of the syringe is shown, an upper end of the syringe 66 being substantially identical to that illustrate in FIG. 1.

The syringe 66 generally comprises a receptacle portion 70, a needle 72 mounted on the receptacle portion for movement in outer and inner directions between extended and extracted positions, needle biasing means 74 for normally urging the needle toward the retracted position, an actuator 76 mounted on the receptacle portion for movement in an inward direction to a position of interference with inner movement of the needle and an outward direction to a position out of interference with such movement of the needle, and an actuator biasing means 78 for normally urging the actuator in its inward direction.

Specifically, the receptacle portion 70 is preferably a hollow cylindrical member terminating at a lower end 80 thereof in a reduced diameter portion 82 by virtue of inclined receptacle wall portion 84. The reduced diameter portion 82 is preferably a substantially solid member which functions as a support for the above-stated needle 72, the needle biasing means 74, the actuator 76 and the actuator biasing means 78, as will be discussed in detail below. Accordingly, the reduced diameter portion 82 will hereinafter sometimes be referred to as "support means."

The reduced diameter portion 82 is provided with a first stepped cylindrical bore 86 extending therethrough along a central longitudinal axis of the receptacle portion 70. The first stepped bore 86 includes relatively large diameter upper bore 88, a relatively small diameter lower bore 90, and an intermediate bore 92 positioned between the upper and lower bores and having a diameter intermediate in size relative to the diameters of the upper and lower bores. The upper, intermediate and lower bores 88, 90, 92 are of a size to receive the needle 72, the diameter of the lower bore 90 being slightly greater than that of the needle.

As shown in detail in FIG. 3, a inner wall 132 of the reduced diameter portion 82 which defines the intermediate bore 92 has extending therefrom a plurality of first flanges 134. The first flanges extend radially about the first inner wall 132 and are positioned adjacent lower bore 90. Each of the first flanges 134 is substantially in the shape of a right triangle, with a small leg 136 of the triangular flange being disposed normal to the inner wall 132 and a hypotenuse 138 of the triangle first flange extending at an acute angle relative to the inner wall. As discussed below in detail, the first flanges 134 function in connection with the needle biasing means 74.

The reduced diameter portion 82 is also provided with a second-stepped bore 94, a central longitudinal axis of which extends along a transverse axis of the receptacle portion 70 which is normal to the longitudinal axis of the first-stepped bore 86. The second stepped bore 94 communicates with the upper bore 88 of the first-stepped bore 86. The second stepped bore 94 includes a relatively-small diameter inner bore 96 and a relatively large diameter outer bore 98. The second stepped bore 94 is of a size to receive the actuator 76, the diameter of the inner bore 96 being slightly greater than that of the actuator as discussed below in detail.

As shown in FIGS. 2 and 4, a plurality of second flanges 100 extend outwardly from another inner wall 102 of the reduced diameter portion 82 defining the outer bore portion 98 of the second stepped bore 94. The second flanges 100 extend radially about the second inner wall 102 and are positioned adjacent outer wall 104 of the reduced diameter portion. In addition, like the first flanges 134, the second flanges 100 are substantially in the shape of a right triangle, with a small leg 106 of the triangular flange being disposed normal to the inner wall 102 and a hypotenuse 108 of the triangular flange extending at an acute angle relative to the inner wall 102. As discussed below in detail, the flanges 100 function to retain the actuator biasing means 78 within the outer bore 98 of the second stepped bore 94.

The receptacle portion 70 and the reduced diameter portion 82 terminating therefrom are preferably made of plastic of a type currently used in the manufacture of prior art syringes and further are integrally formed together by injection molding techniques also currently known.

The needle 72 has upper and lower ends 110, 112. A first collar 114, disc-like in configuration, is fixedly mounted on the needle upper end. The collar 114 has a central opening 115 for receiving the needle 72. The collar is preferably made of plastic, the needle being made of metal. The collar 114 is secured in place relative to the needle 72 by suitable fastening means or by a friction mounting of the collar and the needle through the opening 115.

A retainer member 144 is provided on a lower surface 146 of the first collar 114 and is adapted to capture a free upper end 148 of the first coil spring 74 which is bent so as to be disposed in parallel relationship to the lower surface 146 of the first collar 114. The retainer member 144 is elongated and is positioned along a radius of the circular first collar 114. Such position of the retainer member 144 relative to the first collar facilitates assembly of the first coil spring to the first collar as will be hereinafter discussed in detail. The retainer member 144 is preferably made of plastic formed integral with the first collar 114. However, it is contemplated that the retainer member 144 may be formed separately from and securely mounted to the first collar 114.

The needle 72 is adapted to be mounted on the reduced diameter portion 82 of the syringe 66 in an extended position of the needle, wherein the upper end 110 of the same is positioned in registry with the first-stepped bore 86, the collar 114 being in registry with the upper bore 88 of the first-stepped bore, and the lower end 112 of the needle extending outwardly from the reduced diameter portion 82. From its extended position, the needle 72 is adapted to be urged inwardly toward its retracted position by the needle biasing means 78 where the needle is housed within the reduced diameter portion 82 and an interior 116 of the receptacle portion 70.

The needle biasing means 78 is in the form of a coil spring (hereinafter sometimes the "first coil spring"). The first coil spring 78 is housed substantially within the intermediate bore portion 92 of the first-stepped bore 86 when the needle 72 is set in its extended position. Specifically, in such position of the needle 72, the first coil spring 78 is compressed and set in sandwiched relationship between a further inner wall 118 of the reduced diameter portion 82 and the collar 114, with a lower portion 119 of the first coil spring 78 positioned below the first flanges 134. The first coil spring 78 normally urges the needle 72 for inward movement relative to the reduced diameter portion 82. The needle 72 and its biasing means 74 are maintained in their extended and compressed conditions by the actuator 76.

The actuator 76 is in the form of a pin having an elongated shaft 120 and a head 122 removably mounted on a outer end 124 of the shaft. An inner portion 126 of the shaft carries a second collar 128.

The actuator shaft 120 is slidably received within the second-stepped bore 94 and is moveable therein relative to the reduced diameter portion between inner and outer positions. In the inner position of the actuator 76, an inner end 130 of the shaft 120 is disposed to interfere with inward retracted movement of the needle 72 by directly engaging the first collar 114. Also, in the inner position of the actuator, the second collar 128 is positioned closely adjacent the inner bore portion 96 of the second stepped 15 bore 94. In the outer position of the actuator 76, the inner end 130 of the shaft 120 is disposed out of a position with interference with inward movement of the needle 72. The head 122 of the actuator is adapted to facilitate movement of the actuator 76 from its inner position to the outer position. The second collar 128 has a diameter slightly smaller than that of the outer bore 98 and has a length sufficient to provide the actuator with stability against substantial lateral movement of the shaft 120 as the actuator is moved between its inner and outer positions. The actuator 76 is normally urged toward its inner position by the actuator biasing means 78.

Like the needle biasing means 74, the actuator biasing means is in the form of a coil spring (hereinafter sometimes the "second coil spring"). The second coil spring 74 is of a diameter to slidably fit within the outer bore portion 98 of the second stepped bore 94 and positioned between the second collar 128 of the actuator and the second flanges 100 on the second inner wall 102. In its expanded condition, the second coil spring 78 preferably has a length slightly greater than the distance between the second flanges 100 and the second collar 128 so as to suitably hold the actuator 76 within the second stepped bore 94 without undue lateral movement therein.

Although not illustrated in the drawings, the head 122 of the actuator 76 is removable and threadably mounted on the outer end 124 of the actuator shaft 120. The removable connection between the head 122 and the shaft 120 facilitates assembly of the second coil spring 78 within the second stepped bore 94 as will be discussed below in detail.

The second collar 128 and the actuator 76 are preferably integrally formed as a one-piece plastic member by an injection molding technique well known in the relevant art.

As illustrated in FIG. 5, the syringe 66 is also provided with a cap 140, an end 142 of which having an inner diameter slightly greater in size than the outer diameter of the reduced diameter portion 82. In this manner, the cap 140 is adapted to slidably mount over the reduced diameter portion to cover the needle lower end 112.

In assembly of the syringe 66 of the invention, to dispose the needle 72 in its extended outer position and the actuator 76 in its inner position to retain the needle in the extended position against the biasing force of the first spring 78, the first spring is inserted through the interior 116 of the receptacle portion 70 and subsequently positioned in registry with the first stepped bore 86 of the reduced diameter portion 82 and specifically in registry with the intermediate bore 94 thereof, with the lower portion 119 of the first coil spring 78 being supported by the inner wall 118 of the reduced diameter portion and positioned behind the first flanges 134 on the inner wall 132. The upper free end 148 of the first coil spring 74 is positioned within the interior 116 of the receptacle portion 70. The slope and configuration of the hypotenuse portions 138 of the first flanges 132 facilitate such insertion of the first spring 78 behind the first flanges, the first spring first deforming slightly as it is pushed over the flanges and then resuming it normal circular, in cross-section, configuration.

The needle 72 is then inserted through the interior 116 of the receptacle portion 70 and through the first coil spring 74, the lower end 112 of the needle first, and subsequently into registry with the first stepped bore 86, with the first collar 114 on the needle upper end 110 being disposed within the upper bore 90 of the first-stepped bore. This latter step in the assembly of the syringe 66 results in compression of the first coil spring 78 and sandwiching of the same between the first collar 114 and the inner wall 118 of the reduced diameter portion 70. It also results in disposition of the needle 72 in its extended outer position. The first collar 114 is then rotated to effect capturing of the upper free 148 end of the spring 74 within the retainer member 144. The first collar 114 may be provided with an upstanding flange (not shown) to facilitate rotation of the collar. As indicated above, the elongated configuration of the retainer member 114, along with its position on the radius of the first collar 114, facilitates mounting of the upper free end 148 of the first coil spring 74 relative to the first collar.

While the needle 72 is retained in its extended outer position against the biasing force of the first coil spring 78, the actuator shaft 120, with the actuator head 122 threadably disconnected therefrom, is placed in registry with the second stepped bore 94, so as to dispose the inner end 130 of the shaft 120 in registry with the inner bore 88 of the first stepped bore 86 and in a position of interference with inward movement of the needle 72 by engaging the first collar 114 thereof. In this position of the actuator 76, the second collar 128 is positioned closely adjacent to the inner bore portion 96 of the second stepped bore 94.

Subsequently, the second coil spring 78 of the actuator biasing means is also positioned registry with the second stepped bore 94 so as to be disposed between the second collar 128 of the actuator 76 and the second flanges 100. The slope and configuration of the hypotenuse portions 108 of the second flanges 100 permit such insertion of the second coil spring, the spring deforming slightly as it is forced over the flanges. When fully inserted within the second stepped bore 94, the second coil spring 78 is fully housed within the outer bore 98 of the second stepped bore an substantially free from forces acting on either end thereof. The actuator head 122 is then threadably mounted on the actuator shaft 20. The cap 140 is then mounted on the reduced diameter portion 82 to cover the needle 72.

It should be noted that while the assembly of the needle 72 relative to the reduced diameter portion 82 has been described as being performed prior to assembly of the actuator 76, the actuator may be assembled prior to assembly of the needle.

Subsequently, the cap 140 is mounted on the reduced diameter portion 82 so as to cover the exposed needle 72.

In operation of the syringe of the present invention, after the same has been used for drawing blood or administering subcutaneous or intra-muscular injection, with the plunger retracted, the needle 72, in its extended outer position, remains in a position for potential inadvertent contact with medical or waste disposal personnel. To reduce the probability of this potential hazard, the needle 72 is set in its retracted position through manipulation of the actuator 76. Specifically, the actuator, through grasping and pulling of the actuator head 122, is drawn outwardly, against the biasing force of the second coil spring 78, to dispose the outer portion of the actuator in a position where it cannot interference with inward movement of the first collar 114 of the needle 72. To move the actuator into a position out of such interference would likely require disposing the outer end 130 of the actuator shaft 120 fully within the inner bore 96 of the second stepped bore 94. This permits the first coil spring 78 to act on the first collar 114 to urge the needle 72 toward its inner retracted position. So disposed, the needle 72 is in a position where inadvertent contact by medical or waste disposal personnel may be avoided.

It should be noted that by virtue of the connection between the first coil spring 74 and the first collar 114, and interaction of the first flanges 134 and the first coil spring, the needle 72 is retained in its retracted position within the interior 16 of the receptacle portion 70 to reduce the possibility of the needle falling from the receptacle portion should the interior thereof be left open.

The cap 140 may then be mounted on the reduced diameter portion 82.

Once again, it is pointed out that while the illustrated embodiment of the invention has been shown in the form of a syringe, the invention may be utilized in conjunction with other medical instruments such as a vaccutainer or other medical instruments employed for various forms of venepuncture subcutaneous and intramuscular injection and administration of I.V. fluids.

While the invention has been described in connection with a preferred embodiment, it will be understood that the invention is not limited to the disclosed embodiment. To the contrary, reasonable variations, alternatives, modifications and equivalents are possible within the spirit and scope of the invention as defined by the appended claims.

I claim:

1. A medical instrument comprising a needle and means for mounting said needle for movement between an extended operative position relative to said medical instrument where said needle is exposed for use and a retracted inoperative position where said needle is covered so as to reduce the likelihood of inadvertent contact with said needle;

wherein said mounting means comprises support means, needle biasing means, and actuating means, said support means mounting said needle in said extended and retracted positions, said needle biasing means being interposed between said support means and said needle and normally urging said needle toward said retracted position, said actuating means being mounted on said support means for movement between inner and outer positions and adapted to be disposed to retain said needle at said extended position in said inner position of said actuating means, said actuating means further being adapted to be disposed out of engagement with said needle when said actuating means is moved toward said outer position to permit said needle biasing means to act on said needle thereby to force said needle to said retracted position;

said actuating means comprising engaging means adapted to be disposed to engage said needle, to retain said needle in said extended position in said inner position of said actuating means, said engaging means being further adapted to be disposed out of engagement with said needle when said actuating means is moved toward said outer position;

said mounting means further comprises actuator biasing means interposed between said actuating means and said support means, and normally urging said actuating means toward said inner position, such that said engaging means is in a position of interference with movement of said needle to said retracted position, said actuating means being adapted to be moved toward said outer position, against forces exerted thereon by said actuator biasing means, to dispose said engaging means out of a position, and wherein said actuating means being movable relative to said support means through a limited axial distance, there being stops provided on said actuating means to prevent it from moving further than said limited axial distance within said support means.

2. A medical instrument according to claim 1, wherein said needle comprises a first abutment member, said needle biasing means comprising a first coil spring interposed between said abutment member and said support means, said engaging means being adapted to be disposed to engage said abutment member to retain said needle in said extended position in said inner position of said actuating means to be disposed out of engagement with said abutment member to permit said first coil spring to act on said abutment member to move said needle to said retracted position when said actuating means is moved toward said outer position.

3. A medical instrument according to claim 2, and further comprising first retaining means interconnecting said support means, said first coil spring and said abutment member to secure said needle relative to said support means in said retracted position of said needle.

4. A medical instrument according to claim 1, wherein said actuating means comprises a shaft and a second abutment member on said shaft, said actuator biasing means comprising a second coil spring interposed between said second abutment member and said support means.

5. A medical instrument comprising a needle and means for mounting said needle for movement between an extended operative position relative to said medical instrument where said needle is exposed for use and a retracted inoperative position where said needle is covered so as to reduce the likelihood of inadvertent contact with said needle;

wherein said mounting means comprises support means, needle biasing means, and actuating means, said support means mounting said needle in said extended and retracted positions, said needle biasing means being interposed between said support means and said needle and normally urging said needle toward said retracted position, said actuating means being mounted on said support means for movement between inner and outer positions and adapted to be disposed to retain said needle at said extended position in said inner position of said actuating means, said actuating means further being adapted to be disposed out of engagement with said needle when said actuating means is moved toward said outer position to permit said needle biasing means to act on said needle thereby to force said needle to said retracted position;

said actuating means comprises engaging means adapted to be disposed to engage said needle, to retain said needle in said extended position in said inner position of said actuating means, said engaging means being further adapted to be disposed out of engagement with said needle when said actuating means is moved toward said outer position;

said needle comprises a first abutment member, said needle biasing means comprising a first coil spring interposed between said abutment member and said support means, said engaging means being adapted to be disposed to engage said abutment member to retain said needle in said extended position in said inner position of said actuating means and to be disposed out of engagement with said abutment member to permit said first coil spring to act on said abutment member to move said needle to said retracted position when said actuating means is moved toward said outer position;

first retaining means interconnecting said support means, said first coil spring and said abutment member to secure said needle relative to said support means in said retracted position of said needle;

said support means comprises a first bore therethrough and a first inner wall defining said first bore, said needle being set in registry with said first bore, said abutment member comprising a first collar mounted on said needle, said first coil spring being in registry with said first bore in circumferential relationship to said needle and further being interposed between said first inner wall and said first collar, said engaging means being adapted to be disposed to engage said first collar to retain said needle in said extended position in said inner position of said actuating means to be disposed out of engagement with said first collar to permit said first coil spring to act on said abutment member to move said needle to said retracted position when said actuating means is moved toward said outer position.

6. A medical instrument according to claim 5, wherein said support means further comprises a second inner wall defining said first bore, said first coil spring comprising upper and lower portions, said first retaining means comprising first flange means on said second inner wall for interengaging said lower portion of said first coil spring and holding said lower portion relative to said support means when said needle is moved to said retracted position, said first retaining means further comprising a retainer member on said first collar, said upper portion of said first coil spring being adapted to be received by said retainer member to hold said first collar relative to said first coil spring thereby to hold said needle relative to said support means when said needle is moved to said retracted position.

7. A medical instrument according to claim 6, wherein said first flange means comprises at least one first flange having a surface disposed at an acute angle relative to said second wall to facilitate mounting of said first coil spring in registry with said first bore during assembly of said medial instrument.

8. A medical instrument according to claim 7, wherein said support means comprises a second bore therein in communication with said first bore, said actuating means being disposed in registry with said second bore, said engaging means being adapted to be set in registry with said first bore and in engagement with said first collar on said needle in said inner position of said actuating means to interfere with movement of said needle to said retracted position.

9. A medical instrument according to claim 8, wherein said mounting means further comprises actuator biasing means interposed between said actuating means and said support means and normally urging said actuating means toward said inner position and said engaging means toward a position of interference with movement of said needle to said retracted position, said actuating means being adapted to be moved toward said outer position against forces exerted thereon by said actuator biasing means to dispose said engaging means out of a position of interference with movement of said needle to said retracted position.

10. A medical instrument according to claim 9, wherein said actuator biasing means comprises a second coil spring, said actuating means comprising a shaft having a second abutment member, said second coil spring being set in registry with said second bore in circumferential relationship to said shaft, said mounting means further comprising second retaining means on a third inner wall of said support means defining said second bore, said second coil spring being interposed between said second abutment member and said second retaining means, said second retaining means being adapted to retain said second coil spring in registry with said second bore when said actuating means is moved toward its outer position.

11. A medical instrument according to claim 10, wherein said second abutment member comprises a second collar on and circumscribing said shaft.

12. A medical instrument according to claim 11, wherein said collar has a peripheral geometry substantially similar to the geometric cross-sectional configuration of said second bore and has a length extending along said shaft a sufficient magnitude so as to provide lateral stability to said actuating means within said second bore.

13. A medical instrument according to claim 12, wherein said second retaining means comprises a second flange means on said third wall of said support means.

14. A medical instrument according to claim 13, wherein said second flange means comprises at least one second flange having a surface disposed at an acute angle relative to said third wall to facilitate mounting of said second coil spring in registry with said second bore during assembly of said medical instrument.

15. A medical instrument according to claim 14, wherein said engaging means comprises an inner end of said shaft.

16. A medical instrument according to claim 15, wherein said shaft comprises an outer end disposed out of registry with said second bore said actuating means further having a handle on said outer end of said shaft for facilitating movement of said actuating means toward said outer position.

17. A medical instrument according to claim 16, wherein said handle is removably mounted on said shaft outer end so as to facilitate mounting of said second coil spring in registry with said second bore in circumferential relationship to said shaft during assembly of said medical instrument.

* * * * *

UNITED STATES PATENT AND TRADEMARK OFFICE
CERTIFICATE OF CORRECTION

PATENT NO. : 5,046,508
DATED : September 10, 1991
INVENTOR(S) : Jonathan Weissler It is certified that error appears in the above-identified patent and that said Letters Patent is hereby corrected as shown below:

In column 10, line 63, please delete "," and add -- of interference with movement of said needle to said retracted position, --.

Signed and Sealed this

Second Day of February, 1993

Attest:

STEPHEN G. KUNIN

*Attesting Officer*     *Acting Commissioner of Patents and Trademarks*